United States Patent
Pinchuk et al.

(10) Patent No.: US 7,837,644 B2
(45) Date of Patent: Nov. 23, 2010

(54) GLAUCOMA IMPLANT DEVICE

(75) Inventors: Leonard Pinchuk, Miami, FL (US); Jean-Marie A. Parel, Miami Shores, FL (US); Francisco Fantes, Key Biscayne, FL (US)

(73) Assignee: Innfocus, LLC, Miami, FL (US)

( * ) Notice: Subject to any disclaimer, the term of this patent is extended or adjusted under 35 U.S.C. 154(b) by 221 days.

(21) Appl. No.: 11/561,956

(22) Filed: Nov. 21, 2006

(65) Prior Publication Data

US 2007/0118066 A1    May 24, 2007

Related U.S. Application Data

(63) Continuation-in-part of application No. 11/004,539, filed on Dec. 3, 2004, now Pat. No. 7,431,709.

(60) Provisional application No. 60/741,514, filed on Dec. 1, 2005.

(51) Int. Cl.
*A61M 5/00*    (2006.01)

(52) U.S. Cl. .................. 604/8; 604/9; 604/264

(58) Field of Classification Search .......... 604/8–10, 604/19, 27–30, 48, 264, 93.01, 94.01; 128/898; 600/561, 573, 579; 606/6, 100, 108
See application file for complete search history.

(56) References Cited

U.S. PATENT DOCUMENTS

| | | | |
|---|---|---|---|
| 4,276,394 A | 6/1981 | Kennedy et al. | |
| 4,316,973 A | 2/1982 | Kennedy | |
| 4,342,849 A | 8/1982 | Kennedy | |
| 4,826,478 A * | 5/1989 | Schocket | 604/8 |
| 4,910,321 A | 3/1990 | Kennedy et al. | |
| 4,929,683 A | 5/1990 | Kennedy et al. | |
| 4,936,825 A | 6/1990 | Ungerleider | |
| 4,946,899 A | 8/1990 | Kennedy et al. | |
| 5,066,730 A | 11/1991 | Kennedy et al. | |
| 5,122,572 A | 6/1992 | Kennedy et al. | |
| RE34,640 E | 6/1994 | Kennedy et al. | |
| 5,397,300 A * | 3/1995 | Baerveldt et al. | 604/8 |

(Continued)

FOREIGN PATENT DOCUMENTS

WO    WO02/47731    6/2002

OTHER PUBLICATIONS

Silastic Rx Medical Grade Tubing. Aug. 8, 2005. Dow Corning. pp. 1-4.*

*Primary Examiner*—Leslie R Deak
*Assistant Examiner*—Philip R Wiest
(74) *Attorney, Agent, or Firm*—Gordon & Jacobson, PC

(57) ABSTRACT

An aqueous humor drainage device having an elongate structure that provides a fluid passageway for diverting aqueous humor from the anterior chamber of the eye. The device is formed from a biocompatible soft polymeric material with a hardness less than Shore 80A. Preferably, the polymeric material includes polyisobutylene and a glassy segment. The device preferably includes at least one fixation member that extends from the elongate structure. In one embodiment, the fixation member is realized by a tab that is spaced apart from the two ends of the elongate structure. In another embodiment, the fixation member is realized by a pair of tines that extend in traverse directions relative to the central axis of the elongate structure. The tines are spaced apart for positioning on opposite sides of the sclera of the eye during use.

13 Claims, 14 Drawing Sheets

U.S. PATENT DOCUMENTS

| | | | |
|---|---|---|---|
| 5,741,331 A * | 4/1998 | Pinchuk | 424/423 |
| 5,968,058 A * | 10/1999 | Richter et al. | 606/166 |
| 6,001,128 A | 12/1999 | Graff et al. | |
| 6,050,970 A | 4/2000 | Baerveldt | |
| 6,102,939 A | 8/2000 | Pinchuk | |
| 6,197,240 B1 | 3/2001 | Pinchuk | |
| 6,468,283 B1 | 10/2002 | Richter et al. | |
| 6,545,097 B2 | 4/2003 | Pinchuk et al. | |
| 6,626,858 B2 | 9/2003 | Lynch et al. | |
| 6,736,791 B1 * | 5/2004 | Tu et al. | 604/8 |
| 6,855,770 B2 | 2/2005 | Pinchuk et al. | |
| 2003/0139729 A1 | 7/2003 | Stegmann et al. | |
| 2003/0236514 A1 * | 12/2003 | Schwarz | 604/890.1 |
| 2004/0193095 A1 | 9/2004 | Shadduck | |
| 2004/0236343 A1 | 11/2004 | Taylor et al. | |

\* cited by examiner

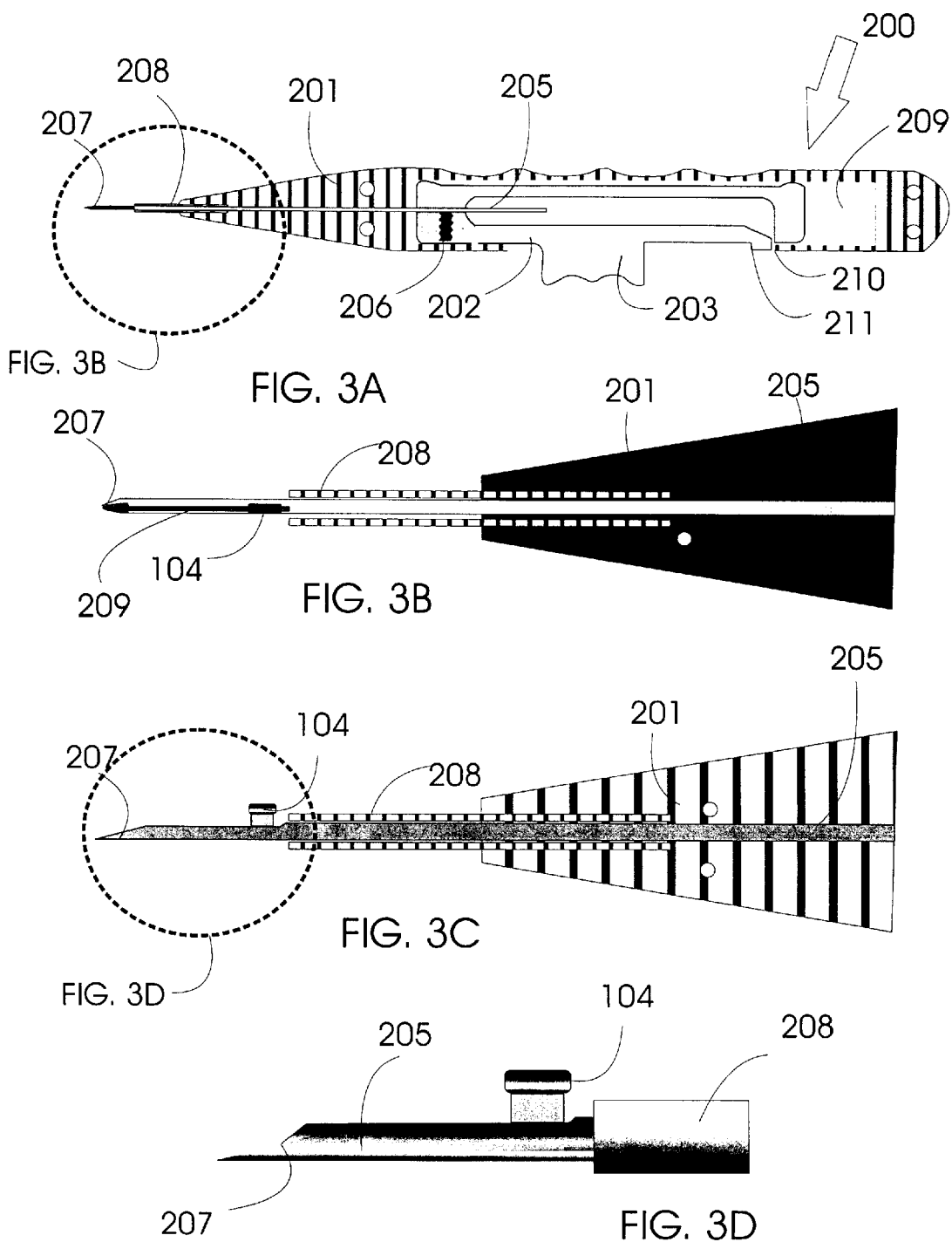

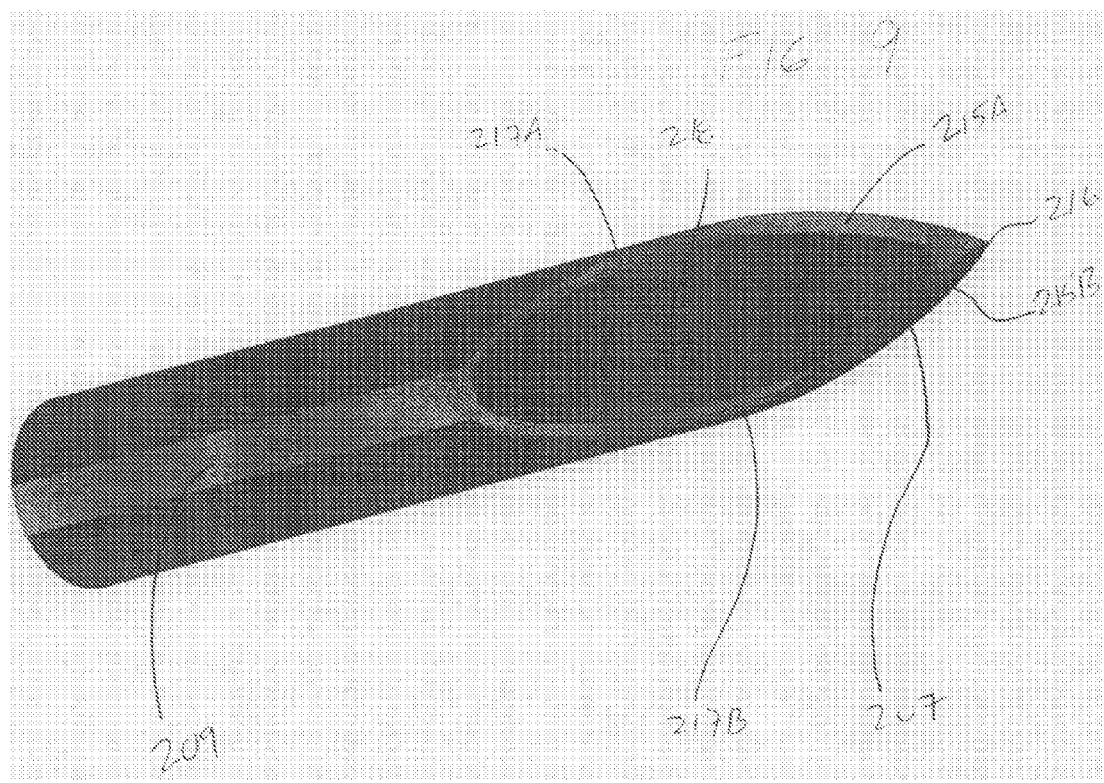

GLAUCOMA IMPLANT DEVICE

CROSS-REFERENCE TO RELATED APPLICATIONS

This application claims priority from U.S. Application No. 60/741,514, filed on Dec. 1, 2005, and is a continuation-in-part of U.S. patent application Ser. No. 11/004,539, filed on Dec. 3, 2004 now U.S. Pat. No. 7,431,709, both of which are hereby incorporated herein by reference in their entireties.

BACKGROUND OF THE INVENTION

1. Field of the Invention

This invention relates broadly to medical devices and materials for reducing intraocular pressure. More particularly, this invention relates to medical devices and materials for diverting aqueous humor out of the anterior chamber through a surgically implanted duct passageway.

2. State of the Art

Glaucoma is a disorder of the optic nerve that usually occurs in the setting of an elevated intraocular pressure (typically referred to as "IOP"). The pressure within the eye increases causing changes in the appearance ("cupping") and function ("blind spots" in the visual field) of the optic nerve. High pressure develops in an eye because of impaired outflow of aqueous. In open-angle glaucoma, the impaired outflow is caused by abnormalities of the drainage system of the anterior chamber. In closed-angle glaucoma, the impaired outflow is caused by impaired access of aqueous to the drainage system. If the pressure within the eye remains sufficiently high for a long enough period of time, total vision loss occurs. Thus, glaucoma is the number one cause of preventable blindness.

As shown in FIG. 1, the eye 10 is a hollow structure that contains a clear fluid called "aqueous humor." Aqueous humor is formed by the ciliary body 12 adjacent the posterior chamber 9 of the eye. The fluid, which is made at a fairly constant rate, then passes around the lens 14, through the pupillary opening in the iris 18 and into the anterior chamber 20. Once in the anterior chamber 20, the fluid drains out of the eye 10 through two different routes. In the "uveoscleral" route, the fluid percolates between muscle fibers of the ciliary body 12. This route accounts for approximately ten percent of the aqueous outflow in humans. The primary pathway for aqueous outflow in humans is through the "canalicular" route that involves the trabecular meshwork (not shown) and Schlemm's canal 24.

The trabecular meshwork and Schlemm's canal 24 are located at the junction between the iris 18 and the sclera 26. This junction is typically referred to as the "angle" 28. The trabecular meshwork is a wedge-shaped structure that runs around the circumference of the eye. It is composed of collagen beams arranged in a three-dimensional sieve-like structure. The beams are lined with a monolayer of cells called trabecular cells. The spaces between the collagen beams are filled with an extracellular substance that is produced by the trabecular cells. These cells also produce enzymes that degrade the extracellular material. Schlemm's canal 24 is disposed adjacent to the trabecular meshwork. The outer wall of the trabecular meshwork coincides with the inner wall of Schlemm's canal 24. Schlemm's canal 24 is a tube-like structure that runs around the circumference of the cornea. In human adults, Schlemm's Canal is believed to be divided by septa into a series of autonomous, dead-end canals. The aqueous fluid travels through the spaces between the trabecular beams of the trabecular meshwork, across the inner wall of Schlemm's canal 24 into the canal, through a series of collecting channels that drain from Schlemm's canal 24 and into the episcleral venous system (not shown).

The tough outer membrane known as the sclera 26 covers all of the eye 10 except that portion covered by the cornea 34, which is the thin, transparent membrane which covers the pupillary opening and the iris 18. The cornea 34 merges into the sclera 26 at a juncture referred to as the limbus 32. A portion of the sclera 26 is covered by a thin tissue called Tenon's membrane 36, which envelopes the bulb of the eye from the optic nerve (not shown) to the ciliary region, and separates the eye from the orbital fat and forms a socket in which the eye moves. Near its front, Tenon's membrane 36 blends into the conjunctiva 30 where it is attached to the ciliary region of the eye as shown.

In a normal patient, aqueous production is equal to aqueous outflow and intraocular pressure remains fairly constant (typically in the 15 to 21 mmHg range). In glaucoma, there is abnormal resistance to aqueous outflow, which manifests itself as increased IOP. Tonometry is the measurement of IOP. In primary open angle glaucoma, which is the most common form of glaucoma, the abnormal resistance is believed to be along the outer aspect of trabecular meshwork and the inner wall of Schlemm's canal 24. Primary open angle glaucoma accounts for approximately eighty-five percent of all glaucoma. Other forms of glaucoma (such as angle closure glaucoma and secondary glaucomas) also involve decreased outflow through the canalicular pathway but the increased resistance is from other causes such as mechanical blockage, inflammatory debris, cellular blockage, etc.

With the increased resistance, the aqueous fluid builds up because it cannot exit fast enough. As the fluid builds up, the IOP within the eye increases. The increased IOP compresses the axons in the optic nerve and also may compromise the vascular supply to the optic nerve. The optic nerve carries vision from the eye to the brain. Some eyes seem more susceptible to IOP than other eyes. While research is investigating ways to protect the nerve from an elevated pressure, the therapeutic approach currently available in glaucoma is to reduce the intraocular pressure.

The clinical treatment of glaucoma is typically carried out in a step-wise manner. Medication often is the first treatment option. Administered either topically or orally, these medications work to either reduce aqueous production or they act to increase outflow. Currently available medications have many serious side effects including: congestive heart failure, respiratory distress, hypertension, depression, renal stones, aplastic anemia, sexual dysfunction and death. Compliance with medication is a major problem, with estimates that over half of glaucoma patients do not follow their correct dosing schedules.

When medication fails to adequately reduce the pressure, laser trabeculoplasty often is performed. In laser trabeculoplasty, thermal energy from a laser is applied to a number of noncontiguous spots in the trabecular meshwork. It is believed that the laser energy stimulates the metabolism of the trabecular cells in some way, and changes the cellular material in the trabecular meshwork. In a large percent of patients, aqueous outflow is enhanced and IOP decreases. However, the effect often is not long lasting and a significant percentage of patients develop an elevated pressure within the years that follow the treatment. The laser trabeculoplasty treatment is typically not repeatable. In addition, laser trabeculoplasty is not an effective treatment for primary open angle glaucoma in patients less than fifty years of age, nor is it effective for angle closure glaucoma and many secondary glaucomas.

If laser trabeculoplasty does not reduce the pressure sufficiently, then incisional surgery (typically referred to as filtering surgery) is performed. With incisional surgery, a hole is made in the sclera 26 adjacent the angle region. This hole allows the aqueous fluid to leave the eye through an alternate route.

The most commonly performed incisional procedure is a trabeculectomy. In a trabeculectomy, a posterior incision is made in the conjunctiva 30. The conjunctiva 30 is rolled forward, exposing the sclera 26 at the limbus 32. A partial scleral flap is made and dissected into the cornea. The anterior chamber 20 is entered beneath the scleral flap, and a section of deep sclera 26 and trabecular meshwork is excised. The scleral flap is loosely sewn back into place. The conjunctiva incision is tightly closed. Post-operatively, the aqueous fluid passes through the hole, beneath the scleral flap and collects in a bleb formed beneath the conjunctiva 30. The fluid then is either absorbed through blood vessels in the conjunctiva 30 or traverses across the conjunctiva 30 into the tear film. Trabeculectomy surgery of this nature is extremely difficult and only a small fraction of ophthalmologists perform this procedure. In addition, it is very time consuming and physicians are not reimbursed for the time it takes to perform the surgery and it is therefore rarely performed.

When trabeculectomy doesn't successfully lower the eye pressure, the next step, and usually the last, is a surgical procedure that implants a device that shunts aqueous humor to control the IOP. One such implant device, as shown in U.S. Pat. No. 6,050,970 to Baerveldt, is a drainage tube that is attached at one end to a plastic plate. The drainage tube is a flow tube between 1.0 and 3.0 French (and preferably with an inner diameter of 0.3 mm and an outer diameter of 0.6 mm). An incision is made in the conjunctiva 30, exposing the sclera 26. The plastic plate is sewn to the surface of the eye posteriorly, usually over the equator. A full thickness hole is made into the eye at the limbus 32, usually with a needle. The tube is inserted into the eye through this hole. The external portion of the tube is covered with either sclera or other tissue. The conjunctiva 30 is replaced and the incision is closed tightly. With this shunt device, aqueous drains out of the eye through the silicone tube to the bleb, which is a thin layer of connective tissue that encapsulates the plate and tube and then to the surface of the eye. Aqueous drains out of the bleb and to the surface of the eye. Deeper orbital tissues then absorb the fluid. The plate typically has a large surface area in order to wick and disperse fluid, which facilitates absorption of fluid in the surrounding tissue. These disks are generally made of silicone rubber, which serves to inhibit tissue adhesion as the plate becomes encapsulated by the connective tissue of the bleb. The disks can be as large as 10 mm in diameter and are irritating to some patients.

Other implant devices are shown in U.S. Pat. No. 6,468,283 to Richter et al. and U.S. Pat. No. 6,626,858 to Lynch et al., respectively. The Richter implant device is a tubular structure that shunts aqueous humor from the anterior chamber to a space between the conjunctiva 30 and the sclera 26. The Lynch implant device is a tubular structure that shunts aqueous humor from the anterior chamber through the trabecular meshwork and into Schlemm's canal 24. These implant devices are described as being formed from silicone, Teflon, polypropylene, stainless steel, etc. These implant devices also typically require precise placement away from the angle and the iris in order to prevent interference with the iris and/or to avoid occlusion of the drainage lumen by ocular tissue (for example, the fibrous tissue of the iris and/or the sclera that may plug the drainage lumen). In addition, such implant devices typically include a unidirectional valve to minimize hypotony (low IOP) in the anterior chamber of the eye. However, the desired flow control provided by such valves is difficult to maintain and are prone to failure. Lastly, these shunt devices are relatively stiff and have been shown to erode through the ocular tissue wall adjacent thereto over time.

Thus, there remains a need in the art to provide an implant device for the treatment of glaucoma that is realized from a biocompatible material which will not encapsulate in the eye and that enables control over IOP without the need for large surface area plates and possibly without the need for unidirectional flow control valves.

SUMMARY OF THE INVENTION

It is therefore an object of the invention to provide an implant device for the treatment of glaucoma that is realized from a biocompatible material that will not encapsulate in the eye, thereby avoiding occlusion of the implant device by ocular tissue and enabling control over IOP without the need for a large diameter plate.

It is a further object of the invention to provide an implant device for the treatment of glaucoma that utilizes a small size duct structure, thereby enabling more flexible and less precise positioning of the duct structure within the ocular cavity and also enabling multiple devices to be implanted, if necessary.

In accord with these objects, which will be discussed in detail below, a surgical implant device for treating glaucoma includes an elongate duct structure that provides a fluid passageway for diverting aqueous humor from the anterior chamber of the eye and at least one fixation member that extends radially outward from the elongate duct structure. In one embodiment, the at least one fixation member is realized by a tab that is spaced apart from the two ends of the elongate duct structure. In other embodiment, the at least one fixation member is realized by a pair of tines that extend in traverse directions relative to the central axis of the elongate duct structure. The tines are spaced apart along the length of the elongate duct structure for positioning on opposite sides of the sclera in the vicinity of the angle of the eye during use. The elongate duct structure and the at least one fixation member are preferably formed from an elastomeric material. In the preferred embodiment, such elastomeric material includes polyisobutylene and a glassy segment. Such material is advantageous in that it will not encapsulate within the ocular environment and thus provides an unobstructed flowpath that diverts aqueous humor from the anterior chamber. Such material also allows for smaller, simpler designs without the need for a large diameter plate commonly used in the prior art designs, and thus promotes quicker healing.

According to the preferred embodiment of the invention, the elongate duct structure is realized from a soft polymeric material with a hardness less than Shore 80A and defines a lumen channel having a diameter in a range from 0.0025 inches to 0.006 inches.

In another aspect of the invention, a surgical tool is provided for inserting a distal portion of the aqueous humor drainage device into the anterior chamber of the eye. Moreover, the surgical implant device and surgical tool are preferably used as part of a surgical method to divert aqueous humor to a pocket region formed between the conjuctiva-sclera and Tenon's membrane.

Additional objects and advantages of the invention will become apparent to those skilled in the art upon reference to the detailed description taken in conjunction with the provided figures.

BRIEF DESCRIPTION OF THE DRAWINGS

FIGS. 3A through 3D are schematic illustrations of an inserter device for deploying the aqueous drainage device of FIGS. 2A and 2B in accordance with the present invention; FIG. 3A is a schematic cross-section of the entire inserter device; FIGS. 3B and 3C are schematic cross-sections of the front portion of the inserter device; and FIG. 3D is a schematic cross-section of the needle tip of the inserter device with the aqueous drainage device loaded therein.

FIG. 9 is a schematic view of an alternate embodiment of the needle tip of the inserter device of FIGS. 3A-3D.

DETAILED DESCRIPTION OF THE PREFERRED EMBODIMENTS

As used herein, the term "distal" is generally defined as in the direction of the eye of the patient, or away from a user of the apparatus/device. Conversely, "proximal" generally means in the direction away from the eye of the patient, or toward the user of the system/apparatus/device.

Figure 1:
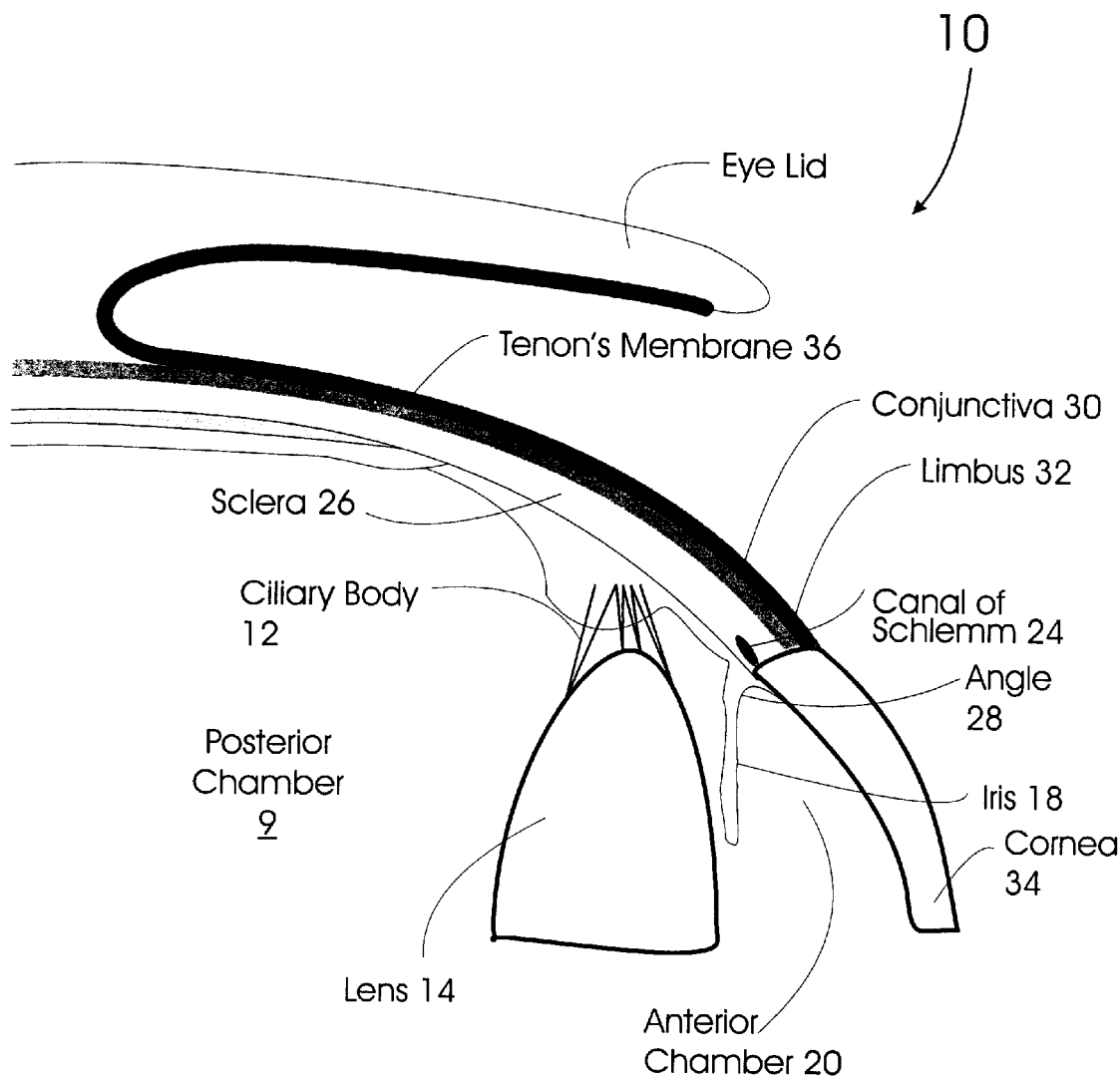
FIG. 1 is a prior art illustration showing anatomic details of the human eye.
Figure 2A:
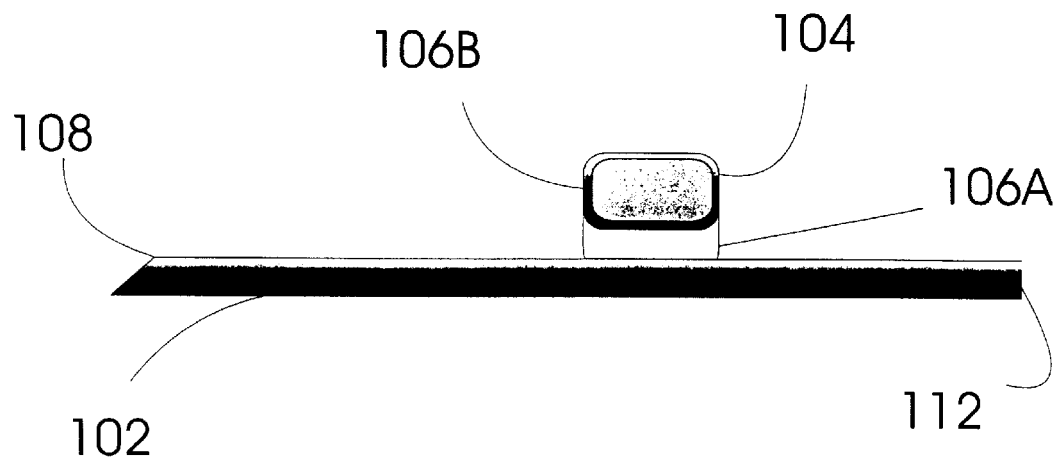
FIG. 2A is a side view of an aqueous drainage device in accordance with the present invention.
Figure 2B:
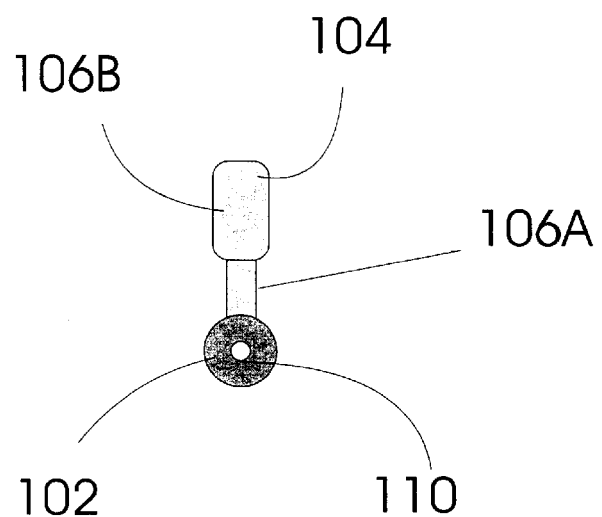
FIG. 2B is a front view of an aqueous drainage device in accordance with the present invention.

Turning now to FIGS. 2A and 2B, there is shown an aqueous drainage tube 100 for treating glaucoma in accordance with the present invention. The aqueous drainage tube 100 includes an elongate tubular body 102 with a fixation tab 104 that extends radially from the central axis of the body 102. Preferably, the fixation tab 104 is positioned at or near the midpoint of the body 102 and includes a narrow portion 106A that extends to a wide portion 106B. The distal end of the body 102 preferably forms a sharp tip 108 as shown in FIG. 2A.

The aqueous drainage tube 100 is preferably formed from a polyolefinic copolymer material having a triblock polymer backbone comprising polystyrene-polyisobutylene-polystyrene, which is herein referred to as "SIBS". SIBS can also be referred to as poly(styrene-b-isobutylene-b-styrene) where b stands for "block". High molecular weight polyisobutylene (PIB) is a soft elastomeric material with a Shore hardness of approximately 10A to 30A. When copolymerized with polystyrene, it can be made at hardnesses ranging up to the hardness of polystyrene, which has a Shore hardness of 100D. Thus, depending on the relative amounts of styrene and isobutylene, the SIBS material can have a range of hardnesses from as soft as Shore 10A to as hard as Shore 100D. In this manner, the SIBS material can be adapted to have the desired elastomeric and hardness qualities. In the preferred embodiment, the SIBS material of the aqueous drainage tube 100 has a hardness less than Shore 80A. Details of the SIBS material is set forth in U.S. Pat. Nos. 5,741,331; 6,102,939; 6,197,240; 6,545,097, which are hereby incorporated by reference in their entirety. The SIBS material of the aqueous drainage tube 100 may be polymerized under control means using carbocationic polymerization techniques such as those described in U.S. Pat. Nos. 4,276,394; 4,316,973; 4,342,849; 4,910,321; 4,929,683; 4,946,899; 5,066,730; 5,122,572; and Re 34,640, each herein incorporated by reference in its entirety. The amount of styrene in the copolymer material is preferably between about 16 mole % to 30 mole % and most preferably between 20 mole % and 27 mole %. The styrene and isobutylene copolymer materials are preferably copolymerized in solvents.

The diameter of the lumen 110 of the aqueous drainage tube 100 is preferably in the range between 0.0025 inches to 0.006 inches. The outer diameter of the aqueous drainage tube 100 is preferably less than 0.02 inches and most preferably on the order of 0.01 inches. The appropriate lumen diameter will vary among patients depending on the IOP of the patient and thus is selected by the physician as desired. Advantageously, this range of small lumen diameters limits aqueous flow through the tube and provides for control over IOP without the need for unidirectional valves. The preferred SIBS material of the aqueous drainage tube 100 provides superb biocompatibility and biostability characteristics. Moreover, animal tests have shown that surprisingly it will not encapsulate in the eye, and thus can be used to provide unobstructed drainage from the anterior chamber of the eye.

It is expected that alternative polymeric materials are suitable for the practice of the present invention. Such alternative polymeric materials preferably include polyisobutylene-based material capped with a glassy segment. The glassy segment provides a hardener component for the elastomeric polyisobutylene. The glassy segment preferably does not contain any cleavable group which will release in the presence of body fluid inside the human eye and cause toxic side effects and cell encapsulation. The glassy segment can be a vinyl aromatic polymer (such as styrene, α-methylstyrene, or a mixture thereof), or a methacrylate polymer (such as methylmethacrylate, ethylmethacrylate, hydroxymethalcrylate, or a mixture thereof). Such materials preferably have a general block structure with a central elastomeric polyolefinic block and thermoplastic end blocks. Even more preferably, such materials have a general structure:

BAB or ABA (linear triblock),
B(AB)$_n$ or a(BA)$_n$ (linear alternating block), or
X-(AB)$_n$ or X-(BA)$_n$ (includes diblock, triblock and other radial block copolymers), where A is an elastomeric polyolefinic block, B is a thermoplastic block, n is a positive whole number and X is a starting seed molecule.

Such materials may be star-shaped block copolymers (where n=3 or more) or multi-dendrite-shaped block copolymers. These materials collectively belong to the polymeric material referred to herein as SIBS material.

Alternatively, the aqueous drainage tube 100 can be realized from another soft elastomeric polymeric material. Preferably, the soft elastomeric polymeric material is biocompatible and biostable within the ocular environment. Moreover, it is preferable that the soft elastomeric polymeric material of the drainage tube 100 not naturally attract leukocytes and/or myofibroblasts, which protects against encapsulation of the tube in the eye, and thus provides unobstructed drainage from the anterior chamber of the eye.

The distal tip 108 of the aqueous drainage tube 100 is preferably inserted into the anterior chamber of the eye with an inserter device 200 as shown in FIGS. 3A to 4G. The inserter device 200 includes a body 201 that supports a slide member 202 having a thumb grip 203 as shown in FIGS. 3A and 3B. The proximal end of a hollow needle 205 is rigidly connected to the slide member 202 preferably by a set screw 206. The slide member 202 is disposed within an interior space 209 of the body 201 and is capable of translation relative to the body 201 in order to translate the needle 205 out (distal movement) and in (proximal movement) along its central axis. An over-tube 208 extends from the nose of the body 201 as shown in FIGS. 3B through 3D. The distal portion of the needle 205 extends from the over-tube 208 and terminates at a sharp tip 207 (FIG. 3D).

The distal portion of the needle 205 includes a guide slot 209 that extends through the annular wall of the needle 205 in a lengthwise manner as best shown in FIG. 3B. The width of the guide slot 209 along most of its length is greater than the width of the narrow portion 106A of the fixation tab 104 and is less than the width of the wide portion 106B of the fixation tab 104. In this manner, the narrow portion 106B of the fixation tab rides within the guide slot 209 during deployment as described below. In FIGS. 3A through 3D, the elongate body 102 of the aqueous drainage tube 100 is loaded within the distal portion of the hollow needle 205.

Figure 4A:
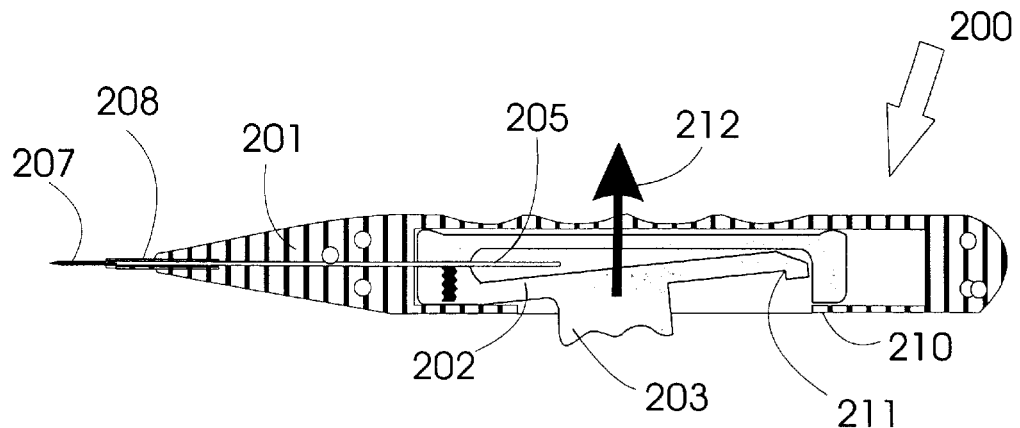
FIGS. 4A through 4G are schematic illustrations of the deployment of the aqueous drainage device of FIGS. 2A and 2B utilizing the inserter device of FIGS. 3A through 3D.

As shown in FIG. 3A, the body 201 includes a stop 210 that cooperates with a locking tab 211 of the slide member 202 to prohibit proximal translation of the slide member 202 and needle 205 in its default configuration. As shown in FIG. 4A, the user can apply an inward pressing force (depicted by the arrow 212) to the thumb grip 203, which causes the locking tab 211 to deflect inward. Such deflection allows the locking tab 211 to clear the stop 210 such that the slide member 202 and needle 205 can translate proximally relative to the body 201.

Figure 4B:
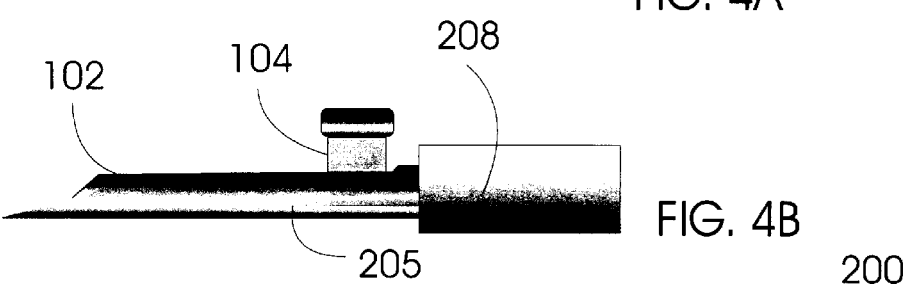

Deployment of the aqueous drainage tube from the inserter 200 is carried out as shown in the sequence of FIGS. 4A through 4G. Initially, the elongate body 102 of the aqueous drainage tube 100 is loaded within the distal portion of the hollow needle 205, and the slide member 202 and needle 205 are locked in place by the locking tab 211 and the stop 210 (FIG. 3A). The user then applies an inward pressing force to the thumb grip 203, which causes the locking tab 211 to deflect inward as shown in FIG. 4A. Such deflection allows the locking tab 211 to clear the stop 210 such that the slide member 202 and needle 205 can translate proximally relative to the body 201. The relative position of the aqueous drainage tube 100 and the hollow needle 205 is shown in FIG. 4B.

Figure 4C:
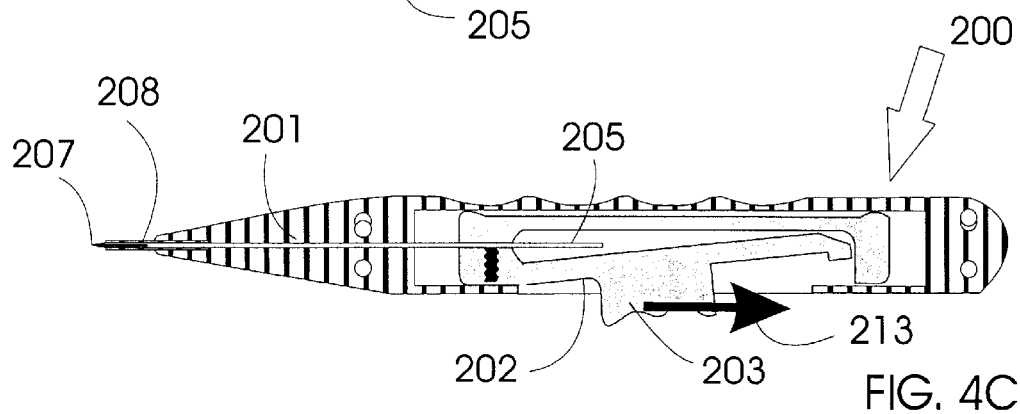
Figure 4D:
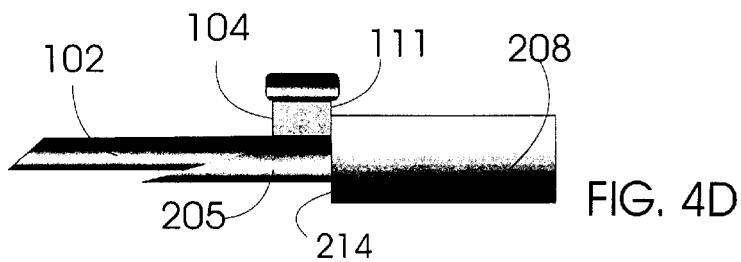

The user then applies a rearward pressing force (depicted by the arrow 213) on the thumb grip 203, which causes the slide member 202 and needle 205 to translate proximal relative to the body 201 as shown in FIG. 4C. During such proximal translation, the proximal edge 111 of the fixation tab 104 butts up against the distal end 214 of over-tube 208 such that the body 102 of the aqueous drainage tube 100 partially slides out of the lumen of the hollow needle 205 through an opening in the tip 207 as shown in FIG. 4D.

Figure 4E:
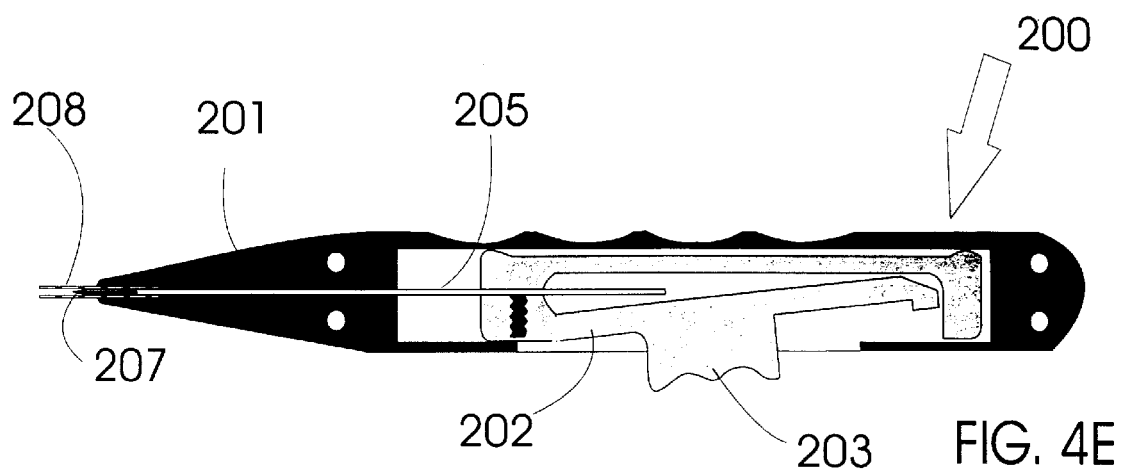
Figure 4F:
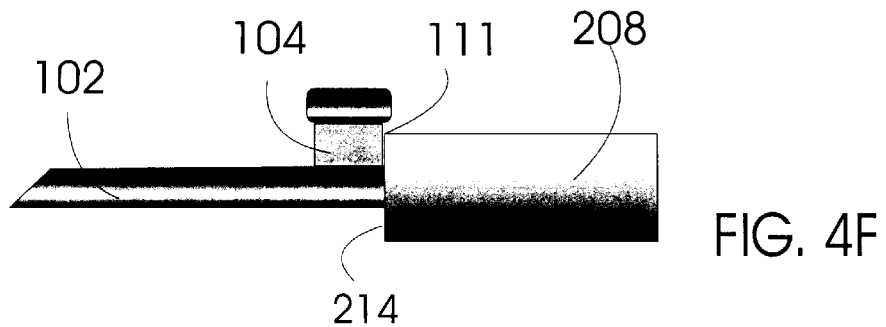

The user continues to apply the rearward pressing force on the thumb grip 203, which causes the slide member 202 and needle 205 to further translate proximal relative to the body 201 as shown in FIG. 4E. In this step, the distal tip 207 of the needle 205 is retracted into the interior of the over-tube 208. During such proximal translation, the proximal edge 111 of the fixation tab 104 remains butted up against the distal end 214 of over-tube 208 such that the body 201 of the aqueous drainage tube 100 is further ejected from the lumen of the hollow needle 205 as best shown in FIG. 4F.

Figure 4G:
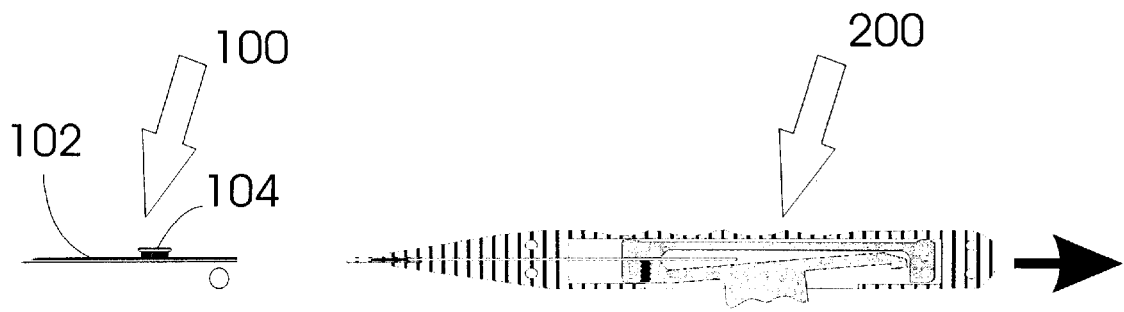

Finally, the user retracts the inserter assembly 200 such that the entire aqueous drainage tube 100 is ejected from the over-tube 208 as shown in FIG. 4G.

The body 201 and slide member 203 of the inserter device 200 can be realized from an engineering plastic such as ABS, Xenoy, Ultem, polycarbonate, rigid polyurethane, polyethylene, polypropylene, nylon and the like. For disposable applications, it is preferred that these components be injection molded. If the inserter device is not to be disposable (i.e., it is sterilizable and reusable), all components can be made from medical grade metals such as stainless steel, galvanized aluminum, gold, platinum, and the like. Lubricant may be applied to the slide member 202 to help it translate from side to side.

Turning now to FIGS. 5A through 5D, there is shown the aqueous drainage tube 100 of the present invention implanted such that its distal tip 108 is positioned within the anterior chamber 20 of the eye and its proximal end 112 is positioned in a pouch 300 formed between Tenon's membrane 36 and the sclera 26. The pouch 300 is closed and a space 302 between Tenon's membrane 36 and the sclera 26 remains in the plane of the pouch 300. The aqueous drainage tube 100 shunts aqueous humor from the anterior chamber 20 to the space 302, which forms a shallow bleb. Aqueous fluid is absorbed into the adjacent tissue and ends up in the venous system in the eye or in the tear film.

Figure 5A:
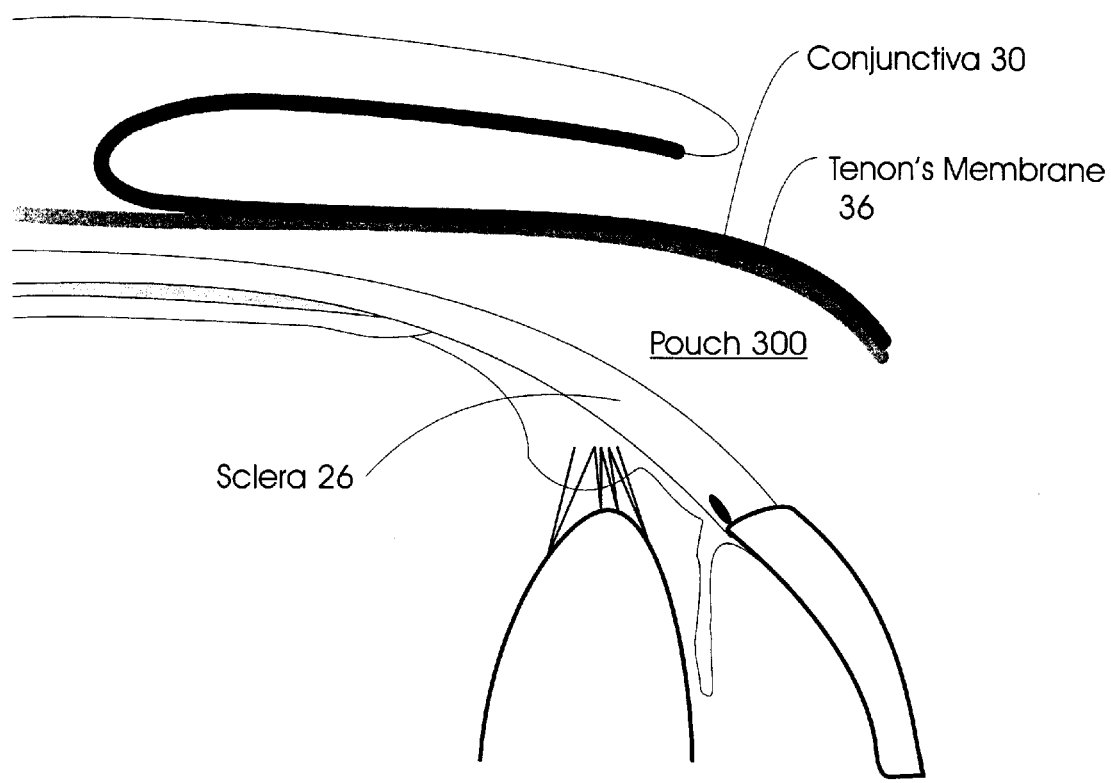
FIGS. 5A through 5D are illustrations showing the aqueous drainage device of FIGS. 2A and 2B implanted into the eye to shunt aqueous humor from the anterior chamber to a space between Tenon's membrane and the sclera of the eye.
Figure 5B:
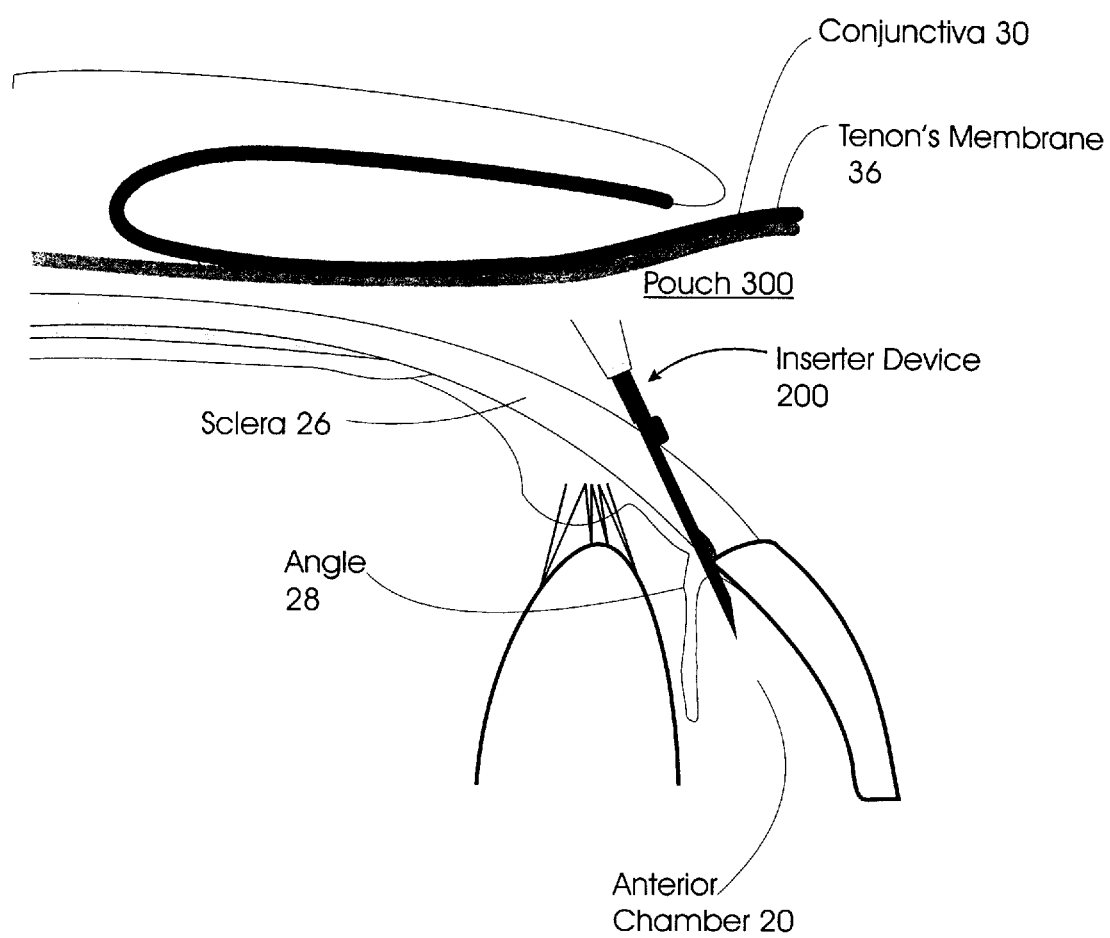
Figure 5C:
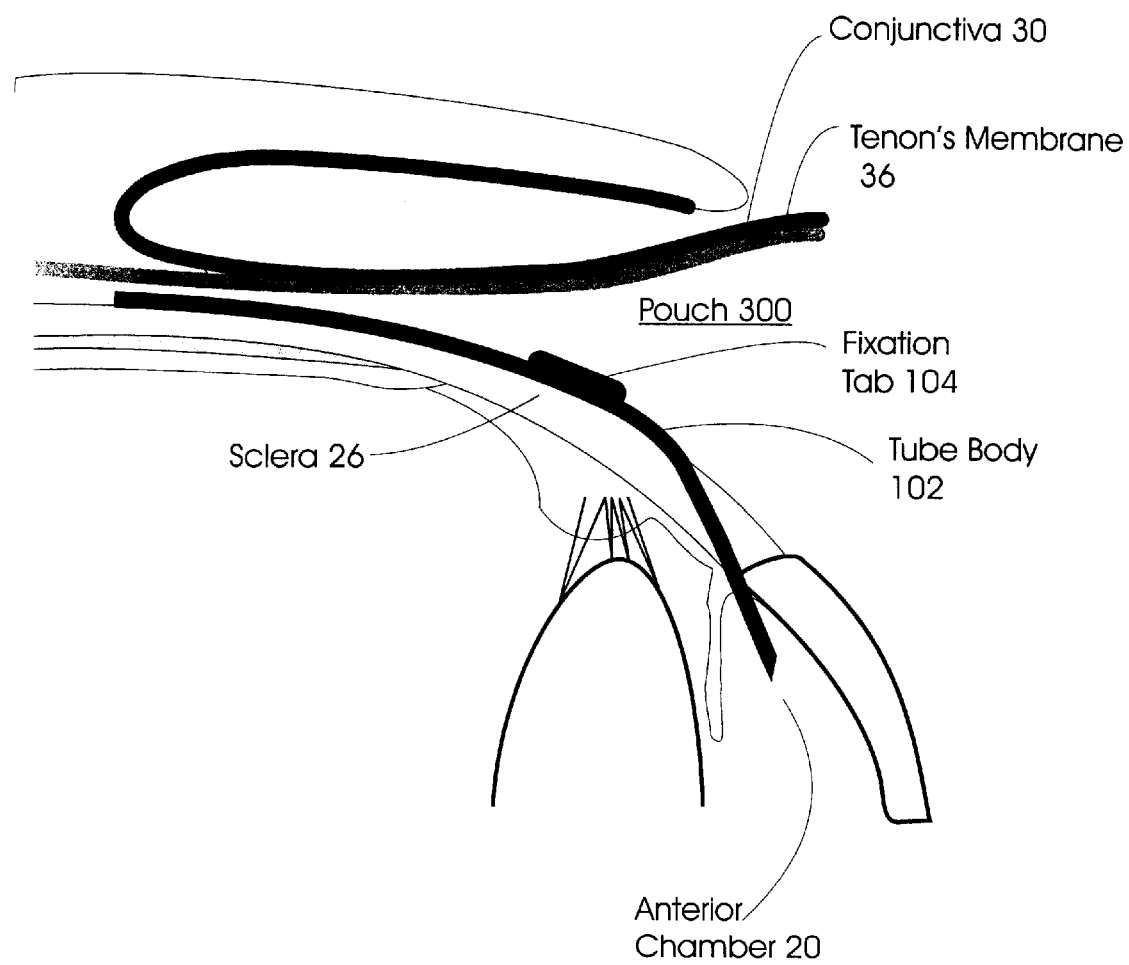
Figure 5D:
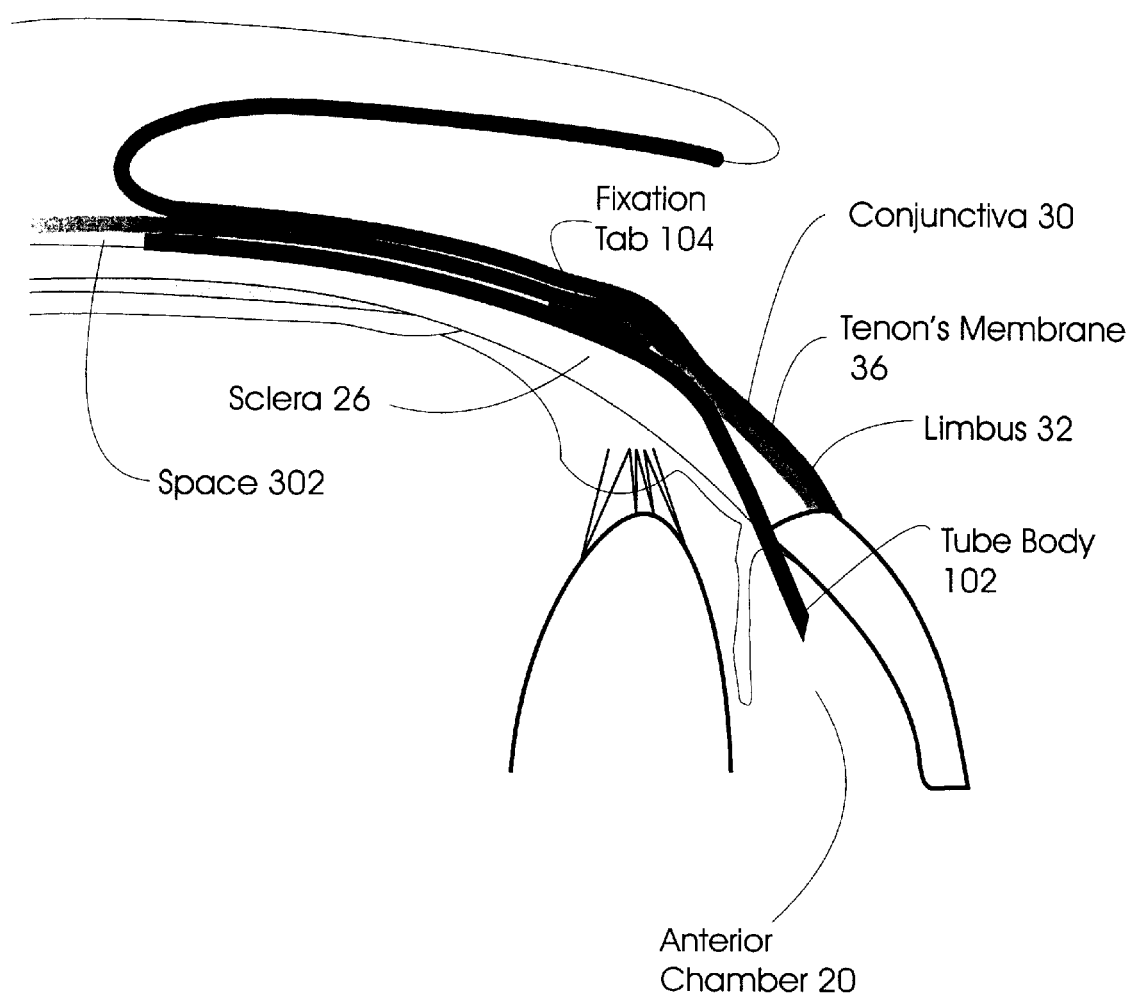

The pouch 300 extends rearward from a location at or near the limbus to the posterior portion of the globe of the eye near the equator of the eye as best shown in FIG. 5B. The pouch 300 is preferably defined by making an incision through Tenon's membrane 36 into the conjuctiva-sclera and then dissecting and separating Tenon's membrane 36 from the sclera 26 over the area of the pouch 300. The distal end 108 of the aqueous drainage tube 100 is inserted through a needle tract the passes through the angle 28 to the anterior chamber 20 of the eye (FIGS. 5B and 5C). The proximal end 112 of the aqueous drainage tube 100 is located within the rear of the pouch 300 (FIG. 5C). After proper positioning of the tube 100, the pouch 300 is closed. A sponge, blotting paper or other suitable carrier loaded with an anti-proliferative agent can be placed within the pouch 300 before it is closed. The anti-proliferative agent may be, for example, mitomycin C or 5-Fuorouracil or other antimetabolites or other suitable drug(s) or compound(s) that releases over time and functions to minimize fibrosis of the conjuctiva-sclera to Tenon's membrane, thereby maintaining the structure of the pouch 300 over an extended period of time. A closed space 302 between Tenon's membrane 36 and the sclera 26 remains in the plane of the pouch 300 (FIG. 5D). Aqueous humor flows from the anterior chamber 20 through the lumen of the tube 100 and into the closed space 302. The closed space 302 prevents bacteria from entering the tube 100 and infecting the eye. Aqueous humor exiting the tube 100 and entering the closed space 302 creates a very shallow bleb. The bleb fluid may filter through the conjunctiva 30 into the tears, and the fluid may be absorbed through the capillaries that interpenetrate the conjunctiva 30. A fraction of the aqueous humor contained in the bleb may potentially seep through the permeable sclera 26 and be absorbed by the choroidal capillaries. The fixation tab 104 of the aqueous drainage tube 100 is preferably positioned near the limbus 32 where the conjunctiva 30 adheres very strongly to the sclera 26, thus sealing the fixation tab 104 along its periphery with time and thus preventing the tube 100 from migrating into, or away from, the anterior chamber 20 of the eye.

Figure 6A:
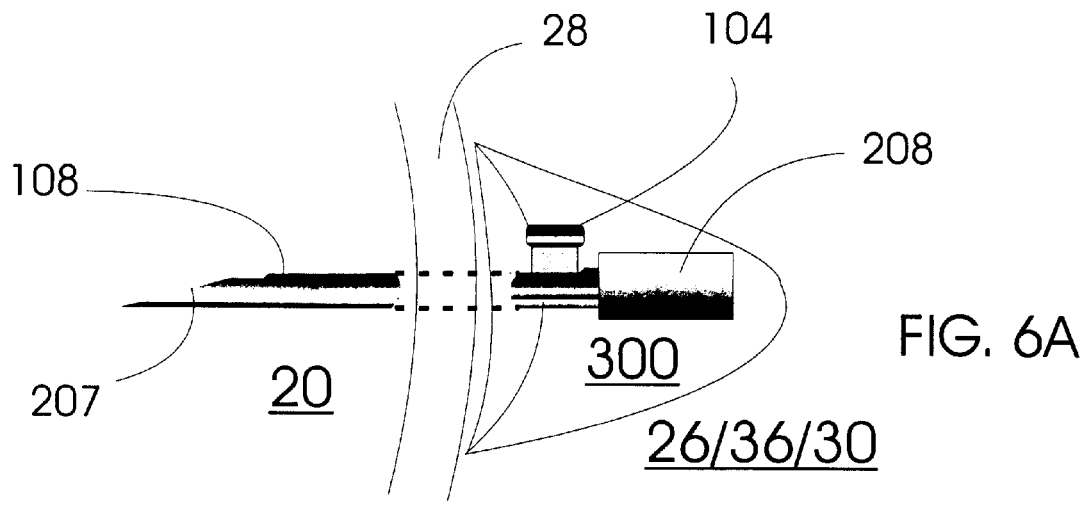
FIGS. 6A through 6C are schematic illustrations of a methodology for implanting the aqueous drainage device of FIGS. 2A and 2B into the eye such that the device shunts aqueous humor from the anterior chamber of the eye to a space defined between Tenon's membrane and the sclera of the eye.
Figure 6B:
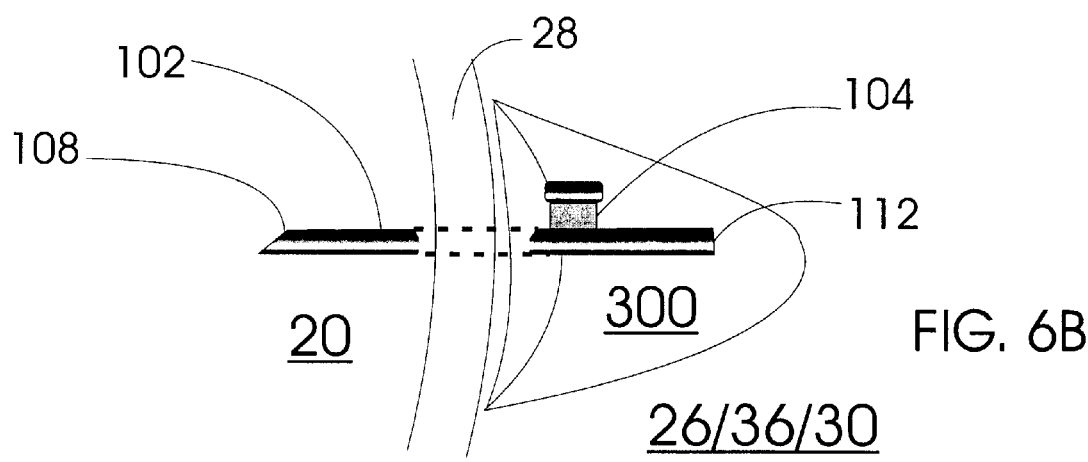
Figure 6C:
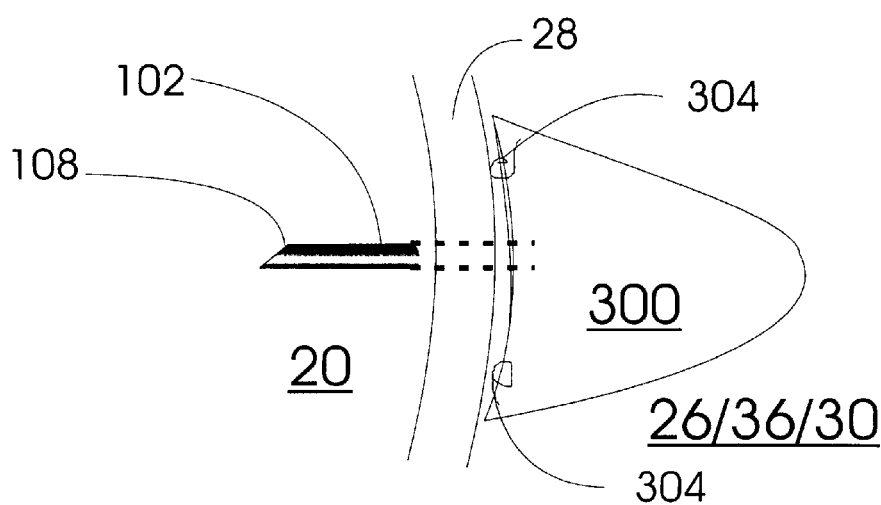

In accordance with the present invention, the aqueous drainage tube 100 is implanted into the position shown in FIGS. 5A through 5D utilizing a method shown in FIGS. 6A through 6C. FIG. 6A shows a very small section of the eye, including the anterior chamber 20, the conjunctiva 30 and underlying sclera 26, and the limbus 32. The pouch 300 is made by disinserting the conjunctiva 30 at the limbus 32 in an incision area 302 less than one quadrant using miniature scissors (Vannas scissors or similar) and dissecting and separating Tenon's membrane 36 from the sclera 26 over a few millimeters. Then, holding the edge of the pouch 300 at its center with toothed forceps, the closed tips of a pair of blunt scissors (e.g. Westcott or similar) are slowly pushed downward toward the eye equator and open up to separate (delaminate) Tenon's membrane 36 from the sclera 26. The scissors are again closed; its tips pushed further forward and reopened to separate a larger area of Tenon's membrane 36. The process is repeated until the tips of the scissors are 17 to 20 mm away from the limbus 32. The pouch 300 thusly created in larger at the equatorial base than at the limbal entry.

The pouch 300 is formed adjacent to the limbus 32. A mark, centered in the middle of the conjunctival opening is made 2 mm behind the limbus edge using a blunt caliper. A tissue ink can be used on the tip of the caliper to increase contrast of the tissue mark. A solution filled syringe equipped with a needle (preferably of 27 gauge) is prepared and air bubbles are removed from the syringe and from the tip. The tip of the needle is then positioned at the mark made on the sclera and a surgical track is fashioned to connect the scleral outer wall to the anterior chamber by pushing the needle is a plane such that the tip of the needle enters the eye through the angle 28 into the anterior chamber 20. In this manner, the needle tract passes through the conjunctiva-sclera in the vicinity of the angle 28 and into the anterior chamber 20. The surgeon may elect to fill the anterior chamber 20 with a pharmacological solution, such as epinephrine. After a few seconds, the needle is slowly retracted. The aqueous drainage tube 100 is loaded and locked in the distal portion of the needle 205 of the inserter device 200, and the sharp tip 207 of the inserter device 200 is inserted into the needle track until its tip 207 exits into the anterior chamber 20 of the eye. The aqueous drainage tube 100 is then deployed from the inserter device 200 as described above with respect to FIGS. 3A through 4G. FIG. 6B shows the position of the tube 100 within the pouch 300 after deployment from the inserter device 200. The pouch 300 is then closed with sutures 304 as shown in FIG. 6C. Instead of sutures, bipolar diathermy coagulation, laser welding or cyanoacrylate can be used to close the pouch 300.

Tissue fixation is always a source of inflammation and the fixation point must be as far away as possible from the implant. To minimize inflammation as well as reduce surgical time, the pouch 300 can also be created by disinsertion of the conjunctiva at the limbus and, starting at one edge of the disinsertion, cutting the conjunctival tissue posteriorly for about 3 mm, thus creating a flap door. After placement of the distal end 112 of the tube 100 in the pouch 300, the freed edge of the conjunctiva 30 is juxtaposed about 2 mm past its original position and held taut with a single suture, or a single laser weld, or a single-point bipolar diathermy coagulation, or with a single dot of cyanoacrylate. The edge of the conjunctiva 30 along the limbus 32 is never treated, but left intact to prevent tissue necrosis that engenders fibrosis. The cornea-limbal epithelium cells will rapidly recover the wound edge (1 hour or less), sealing the conjunctival limbus.

A sponge, blotting paper or other suitable carrier loaded with one or more therapeutic agents can be placed within the pouch 300 before it is closed. Such therapeutic agent(s) release over time and minimizes fibrosis of Tenon's membrane to the sclera, thereby preventing re-lamination and closure of the bleb space 302. The therapeutic agents(s) can include cytostatic agents (i.e., anti-proliferation agents that prevent or delay cell division, for example, by inhibiting replication of DNA, and/or by inhibiting spindle fiber formation, and/or by inhibiting cell migration) or other agents that minimize fibrosis or blood clots. Examples of such therapeutic agents are described below.

Alternatively, the polymeric aqueous humor drainage device 100 (or parts thereof) can be loaded with one or more therapeutic agents that release over time and minimize fibrosis of the Tenon's membrane to the sclera, thereby preventing re-lamination and closing of the bleb space 302. The therapeutic agents(s) loaded into the device 100 can include cytostatic agents (i.e., anti-proliferation agents that prevent or delay cell division, for example, by inhibiting replication of DNA, and/or by inhibiting spindle fiber formation, and/or by inhibiting cell migration) or other agents that minimize fibrosis or blood clots. Examples of such therapeutic agents follow.

Representative examples of therapeutic agents include the following: Visudyne, Lucentis (rhuFab V2 AMD), Combretastatin A4 Prodrug, SnET2, H8, VEGF Trap, Cand5, LS 11 (Taporfin Sodium), AdPEDF, RetinoStat, Integrin, Panzem, Retaane, Anecortave Acetate, VEGFR-1 mRNA, ARGENT cell-signalling technology, Angiotensin II Inhibitor, Accutane for Blindness, Macugen (PEGylated aptamer), PTAMD, Optrin, AK-1003, NX 1838, Antagonists of avb3 and 5, Neovastat, Eos 200-F and any other VEGF inhibitor.

Other therapeutic agents can be used such as: mitomycin C, 5-fluorouracil, corticosteroids (corticosteroid triamcinolone acetonide is most common), modified toxins, methotrexate, adriamycin, radionuclides (e.g., such as disclosed in U.S. Pat. No. 4,897,255, herein incorporated by reference in it entirety), protein kinase inhibitors (including staurosporin, which is a protein kinase C inhibitor, as well as a diindoloalkaloids and stimulators of the production or activation of TGF-beta, including tamoxifen and derivatives of functional equivalents, e.g., plasmin, heparin, compounds capable of reducing the level or inactivating the lipoprotein Lp(a) or the glycoprotein apolipoprotein(a) thereof), nitric oxide releasing compounds (e.g., nitroglycerin) or analogs or functional equivalents thereof, paclitaxel or analogs or functional equivalents thereof (e.g., taxotere or an agent based on Taxol®, whose active ingredient is paclitaxel), inhibitors of specific enzymes (such as the nuclear enzyme DNA topoisomerase II and DAN polymerase, RNA polymerase, adenl guanyl cyclase), superoxide dismutase inhibitors, terminal deoxynucleotidyl-transferas, reverse transcriptase, antisense oligonucleotides that suppress cell proliferation, angiogenesis inhibitors (e.g., endostatin, angiostatin and squalamine), rapamycin, cerivastatin, and flavopiridol and suramin and the like.

Other examples of therapeutic agents include the following: peptidic or mimetic inhibitors, such as antagonists, agonists, or competitive or non-competitive inhibitors of cellular factors that may trigger proliferation of cells or pericytes (e.g., cytokines (for example, interleukins such as IL-1), growth factors (for example, PDGF, TGF-alpha or -beta, tumor necrosis factor, smooth muscle- and endothelioal-derived growth factors such as endothelin or FGF), homing receptors (for example, for platelets or leukocytes), and extracellular matrix receptors (for example, integrins).

Representative examples of useful therapeutic agents in the category of agents that address cell proliferation include: subfragments of heparin, triazolopyrimidine (for example, trapidil, which is a PDGF antagonist), lovastatin; and prostaglandins E1 or I2.

Several of the above and numerous additional therapeutic agents appropriate for the practice of the present invention are disclosed in U.S. Pat. Nos. 5,733,925 and 6,545,097, both of which are herein incorporated by reference in their entirety.

If desired, a therapeutic agent of interest can be provided at the same time as the polymer from which the device 100 is realized, for example, by adding it to a polymer melt during thermoplastic processing or by adding it to a polymer solution during solvent-based processing. Alternatively, a therapeutic agent can be provided after formation of the device or device portion. As an example of these embodiments, the therapeutic agent can be dissolved in a solvent that is compatible with both the device polymer and the therapeutic agent. Preferably, the device polymer is at most only slightly soluble in this solvent. Subsequently, the solution is contacted with the device or device portion such that the therapeutic agent is loaded (e.g., by leaching/diffusion) into the copolymer. For this purpose, the device or device portion can be immersed or dipped into the solution, the solution can be applied to the device or component, for example, by spraying, printing dip coating, immersing in a fluidized bed and so forth. The device or component can subsequently be dried, with the therapeutic agent remaining therein.

In another alternative, the therapeutic agent may be provided within a matrix comprising the polymer of the device. The therapeutic agent can also be covalently bonded, hydrogen bonded, or electrostatically bound to the polymer of the device. As specific examples, nitric oxide releasing functional groups such as S-nitroso-thiols can be provided in connection with the polymer, or the polymer can be provided with charged functional groups to attach therapeutic groups with oppositely charged functionalities.

In yet another alternative embodiment, the therapeutic agent can be precipitated onto one or more surfaces of the device or device portion. These one or more surface(s) can be subsequently covered with a coating of polymer (with or without additional therapeutic agent) as described above.

Hence, when it is stated herein that the polymer is "loaded" with therapeutic agent, it is meant that the therapeutic agent is associated with the polymer in a fashion like those discussed above or in a related fashion.

In some instances a binder may be useful for adhesion to a substrate. Examples of materials appropriate for binders in connection with the present invention include silanes, titanates, isocyanates, carboxyls, amides, amines, acrylates hydroxyls, and epoxides, including specific polymers such as EVA, polyisobutylene, natural rubbers, polyurethanes, siloxane coupling agents, ethylene and propylene oxides.

It also may be useful to coat the polymer of the device (which may or may not contain a therapeutic agent) with an additional polymer layer (which may or may not contain a therapeutic agent). This layer may serve, for example, as a boundary layer to retard diffusion of the therapeutic agent and prevent a burst phenomenon whereby much of the agent is released immediately upon exposure of the device or device portion to the implant site. The material constituting the coating, or boundary layer, may or may not be the same polymer as the loaded polymer. For example, the barrier layer may also be a polymer or small molecule from the following classes: polycarboxylic acids, including polyacrylic acid; cellulosic polymers, including cellulose acetate and cellulose nitrate; gelatin; polyvinylpyrrolidone; cross-linked polyvinylpyrrolidone; polyanhydrides including maleic anhydride polymers; polyamides; polyvinyl alcohols; copolymers of vinyl monomers such as EVA (ethylene-vinyl acetate copolymer); polyvinyl ethers; polyvinyl aromatics; polyethylene oxides; glycosaminoglycans; polysaccharides; polyesters including polyethylene terephthalate; polyacrylamides; polyethers; polyether sulfone; polycarbonate; polyalkylenes including polypropylene, polyethylene and high molecular weight polyethylene; halogenated polyalkylenes including polytetrafluoroethylene; polyurethanes; polyorthoesters; polypeptides, including proteins; silicones; siloxane polymers; polylactic acid; polyglycolic acid; polycaprolactone; polyhydroxybutyrate valerate and blends and copolymers thereof; coatings from polymer dispersions such as polyurethane dispersions (BAYHDROL®, etc.); fibrin; collagen and derivatives thereof; polysaccharides such as celluloses, starches, dextrans, alginates and derivatives; and hyaluronic acid.

Copolymers and mixtures of the above are also contemplated.

It is also possible to form the aqueous humor drainage device (or device portion) with blends by adding one or more of the above or other polymers to a block copolymer. Examples include the following:

blends can be formed with homopolymers that are miscible with one of the block copolymer phases. For example, polyphenylene oxide is miscible with the styrene blocks of polystyrene-polyisobutylene-polystyrene copolymer. This should increase the strength of a molded part or coating made from polystyrene-polyisobutylene-polystyrene copolymer and polyphenylene oxide.

blends can be made with added polymers or other copolymers that are not completely miscible with the blocks of the block copolymer. The added polymer or copolymer may be advantageous, for example, in that it is compatible with another therapeutic agent, or it may alter the release rate of the therapeutic agent from the block copolymer (e.g., polystyrene-polyisobutylene-polystyrene copolymer).

blends can be made with a component such as sugar (see list above) that can be leached from the device or device portion, rendering the device or device component more porous and controlling the release rate through the porous structure.

The release rate of therapeutic agent from the therapeutic-agent-loaded polymers of the present invention can be varied in a number of ways. Examples include:

varying the molecular weight of the block copolymers;

varying the specific constituents selected for the elastomeric and thermoplastic portions of the block copolymers and the relative amounts of these constituents;

varying the type and relative amounts of solvents used in processing the block copolymers;

varying the porosity of the block copolymers;

providing a boundary layer over the block copolymer; and blending the block copolymer with other polymers or copolymers.

Moreover, although it is seemingly desirable to provide control over the release of the therapeutic agent (e.g., as a fast release (hours) or as a slow release (weeks)), it may not be necessary to control the release of the therapeutic agent. In such embodiments, one or more of the therapeutic drug agents described herein (e.g., an antiproliferative agent derived from mitomycin C or 5-fluorouracil) may be injected into the pouch at the time of surgery.

Figure 7A:
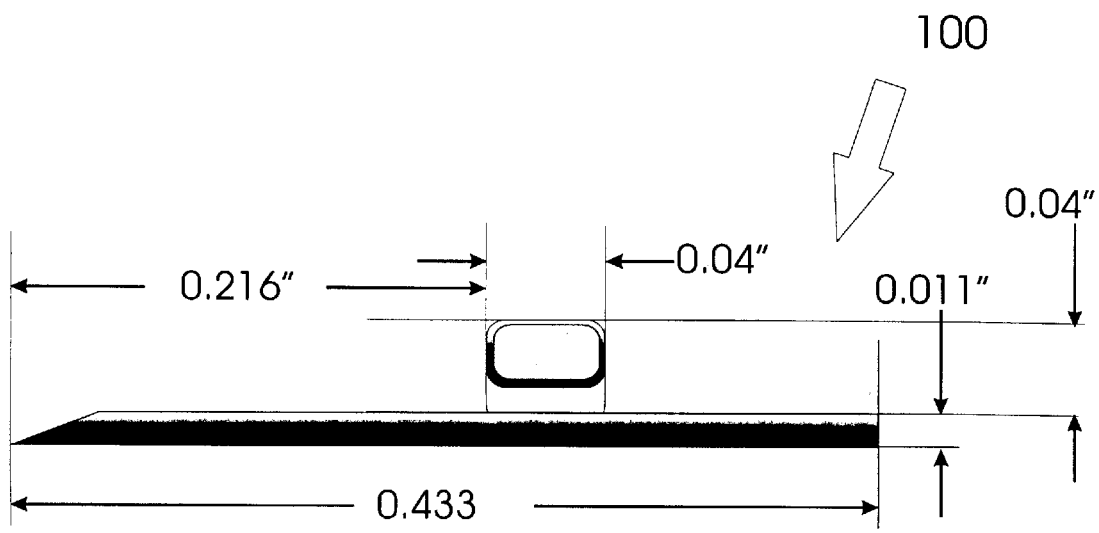
FIGS. 7A and 7B are schematic views of the aqueous drainage device of FIGS. 2A and 2B, which illustrate the dimensions of an exemplary embodiment of the device.
Figure 7B:
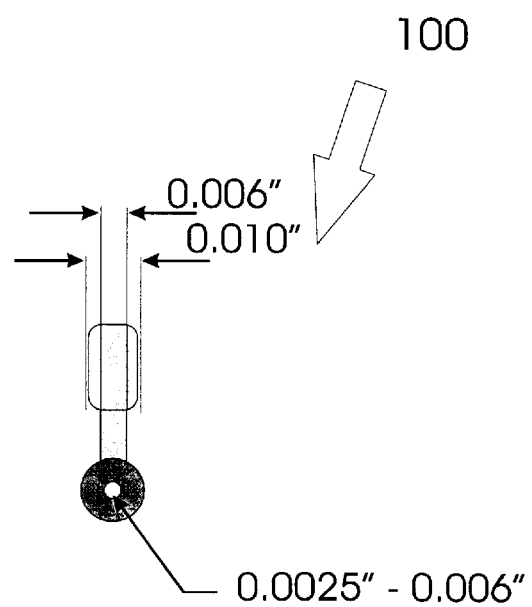

FIGS. 7A and 7B illustrate the dimensions of an exemplary embodiment of the aqueous drainage tube 100 of the present invention.

FIG. 8A through 8G illustrate an alternate design of an aqueous drainage device in accordance with the present invention. The device 100' is meant to prevent migration of the device 100' into and outside of the eye immediately upon implantation. As show in FIGS. 8A and 8B, the device 100' includes an elongate hollow tubular member 301 with the same construction and dimensions as the tubular member 102 described above. Two fixation tines 302, 303 are attached to the tubular member 301 such that they extend transverse thereto. Aqueous humor is meant to flow through the hollow tubular member 301 in the direction of the arrow 304. The fixation tine 302 is disposed near the entrance to the hollow tubular member 301. The fixation tine 303 is preferably disposed near the midpoint of the hollow tubular member 301.

The entire device 100' is preferably realized from soft elastomeric SIBS material with a hardness less than Shore 80A. The preferred SIBS material of the device 100' provides superb biocompatibility and biostability characteristics. Moreover, animal tests have shown that surprisingly it will not encapsulate in the eye, and thus can be used to provide unobstructed drainage from the anterior chamber of the eye. Alternatively, the device 100' can be realized from another soft elastomeric polymeric material. Preferably, the soft elastomeric polymeric material is biocompatible and biostable within the ocular environment. Moreover, it is preferable that the soft elastomeric polymeric material of the device 100' not naturally attract leukocytes and/or myofibroblasts, which protects against encapsulation of the tube in the eye, and thus provides unobstructed drainage from the anterior chamber of the eye.

Figure 8A:
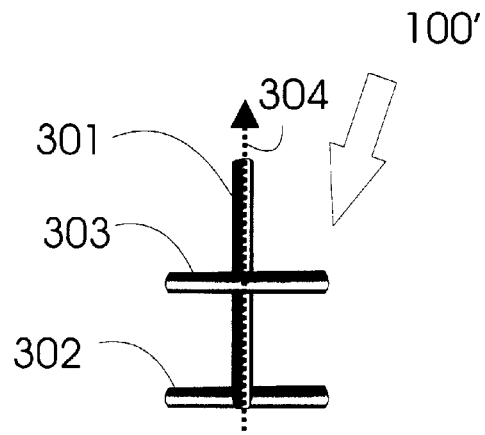
FIGS. 8A through 8G are schematic illustrations of an alternate aqueous drainage device in addition to operations that utilize an inserter device for deploying such aqueous drainage device into the eye in accordance with the present invention.
Figure 8B:
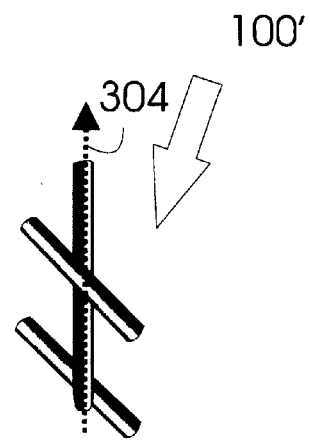
Figure 8C:
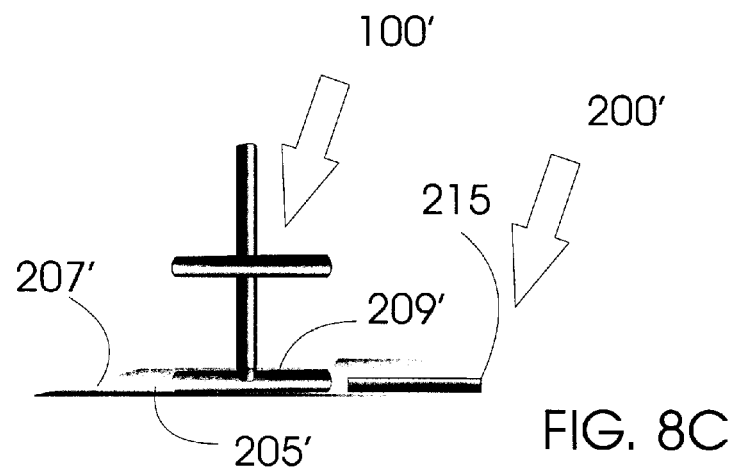

As shown in FIG. 8C, the tine 302 is inserted into a slot 209' that extends along the distal portion of the tip 205' of an inserter 200'. The inserter 200' is similar to the inserter 200 described above. However, in lieu of the over-tube 8 a plunger 215 is connected to the slide member (not shown). The needle 205' is held stationary by fixing it permanently to the body (not shown) of the inserter 200'. The plunger 215 is capable of distal translation relative to the inserter body by applying an axial pushing force to the thumb grip (not shown) of the slide member. A locking mechanism, similar to the lock and stop described above, may be provided to inhibit such distal translation until the user presses on the thumb grip. The aqueous drainage device 100' is deployed by applying an axial pushing force in the distal direction to the thumb grip of the slide member, which causes the plunger 215 to move distally and push against the tine 302 of the device 100', thereby ejecting the device 100' from the tip 207' of the inserter 200'. The tip 207' is preferably realized by two sharp cutting edges that extend to blunt rounded edges, which terminate proximally at the guide slot 209' in the manner shown in FIG. 3E and discussed above in detail.

Figure 8D:
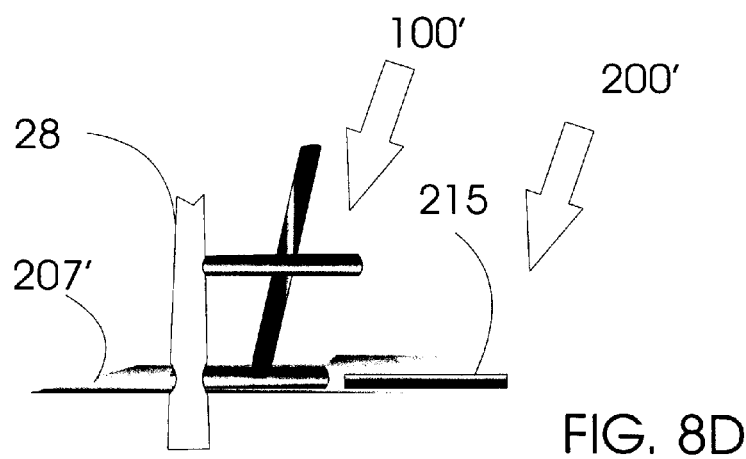
Figure 8E:
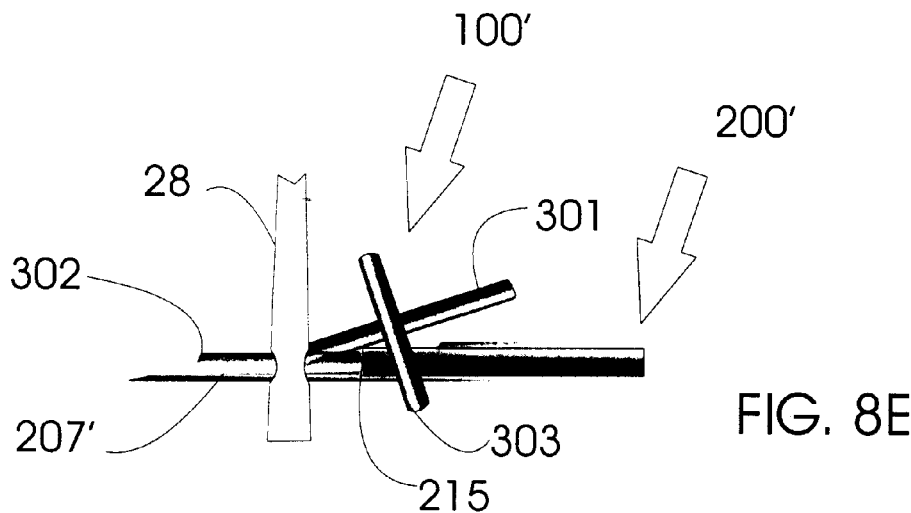
Figure 8F:
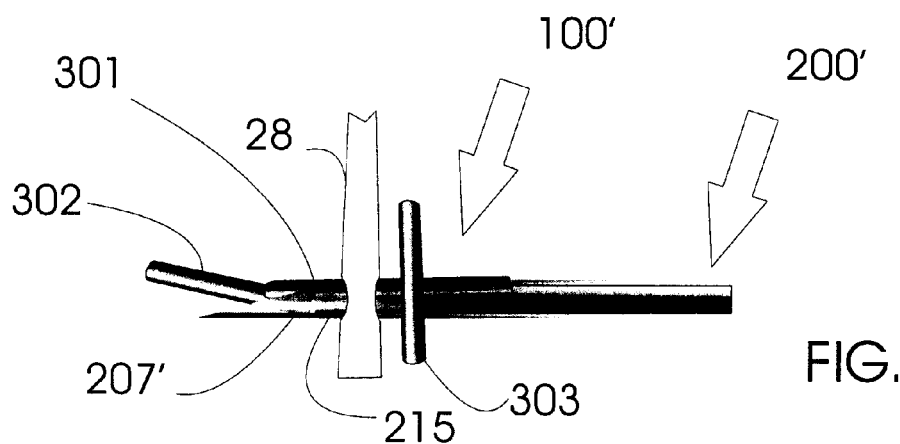
Figure 8G:
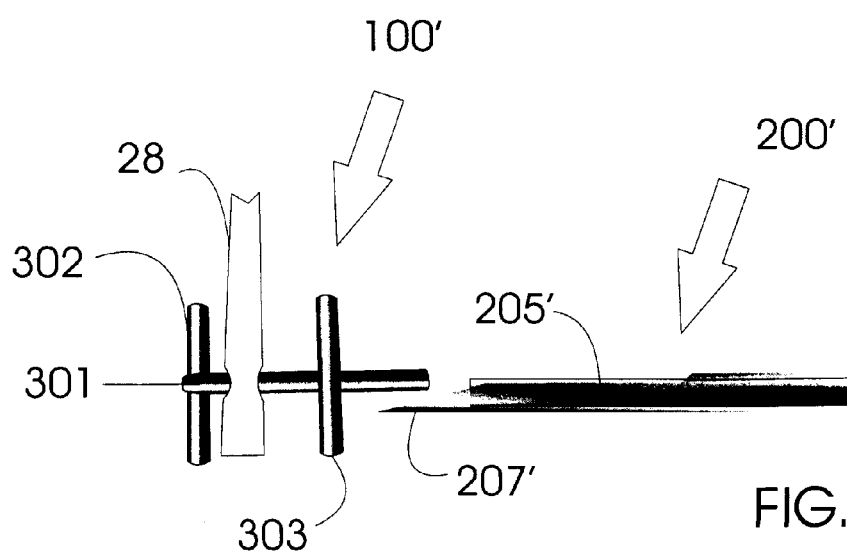

FIG. 8D shows the tip 207' of the inserter 200' inserted into the anterior chamber 20 through the angle 28 via a pouch defined between Tenon's membrane 36 and the sclera 26 (FIG. 5A). The device 100' is deployed by applying an axial pushing force in the distal direction to the thumb grip of the slide member, which causes the plunger 215 to move distally and push against the tine 302 of the device 100', thereby ejecting the device 100' from the tip 207' in the manner shown in FIGS. 8E through 8G. The pushing action of the plunger 215 first causes the tine 302 to pass through the limbus passageway defined by the needle tip 207' of the inserter 200' as shown in FIG. 8E. The continued pushing action of the plunger 215 then causes the bottom portion of the hollow tubular member 301 to pass through the limbus passageway as shown in FIG. 8F. The device 100' is then retracted proximally, which causes the tine 303 and the top portion of the hollow tubular member 301 to be ejected from the needle tip 207' of the inserter 200' as shown in FIG. 8G. In the deployed configuration, the two tines 302, 303 are disposed on opposite sides of the sclera in the vicinity of the angle 28 as shown and thus prevent migration of the device 100' into and outside of the eye immediately upon implantation. After proper positioning of the tube 100', the pouch is closed. A closed space between Tenon's membrane 36 and the sclera 26 remains in the plane of the pouch (FIG. 5D). Aqueous humor flows from the anterior chamber 20 through the lumen of the tube 100' and into this closed space. The closed space prevents bacteria from entering the tube 100' and infecting the eye. Aqueous humor exiting the tube 100' and entering the closed space creates a very shallow bleb. The bleb fluid may filter through the conjunctiva into the tears, and the fluid may be absorbed through the capillaries that interpenetrate the conjunctiva. A fraction of the aqueous humor contained in the bleb may potentially seep through the permeable sclera 26 and be absorbed by the choroidal capillaries. A sponge, blotting paper or other suitable carrier loaded with one or more therapeutic agents can be placed within the pouch before it is closed. Such therapeutic agent(s) release over time and minimize fibrosis of the sclera to Tenon's membrane, thereby preventing re-lamination and closing of the bleb space. Alternatively, the polymeric aqueous humor drainage device 100' (or parts thereof) can be loaded with such therapeutic agents. The therapeutic agents(s) loaded into the device 100' can include any one of the therapeutic agents as described above.

In an alternate embodiment shown in FIG. 9, the sharp tip 207 of the needle 210 may be realized by two sharp cutting edges 215A, 215B that extend proximally and radially outward from a distal-most sharp point 216, which is aligned along the central axis of the body 102. The proximal end of the edges 215A, 215B extend to arcuate blunt rounded edges 217A, 217B that terminate proximally at the guide slot 209. The sharp edges 215A, 215B and the rounded edges 217A, 217B outline an opening 218 through the annular wall of the hollow body 201 into the lumen of the hollow body as shown. The sharp point 216 and the sharp cutting edges 215A, 215B facilitate piercing the eye tissue at the desired insertion point in order to form the needle tract that leads through the eye tissue into the anterior chamber. The blunt rounded edges 217A, 217B facilitate the slidable movement of the needle tip 207 through the needle tract and into the anterior chamber of the eye as discussed above. It is contemplated that this design does not require a separate needle to form the needle tract as described above. In other words, the same needle can be used to form the needle tract and deploy the aqueous humor drainage device therethrough.

There have been described and illustrated herein several embodiments of glaucoma implant devices that divert aqueous humor from the anterior chamber of the eye and surgical methods associated therewith. While particular embodiments of the invention have been described, it is not intended that the invention be limited thereto, as it is intended that the invention be as broad in scope as the art will allow and that the specification be read likewise.

Thus, while particular methods of manufacture have been disclosed, it will be understood that other manufacture methods can be used. For example, because the copolymer materials described herein have a thermoplastic character, a variety of standard thermoplastic processing techniques can be used to for the devices described herein. Such techniques include compression molding, injection molding, blow molding, spinning, vacuum forming and calendaring, and extrusion into tubes and the like. Such devices can also be made using solvent-based techniques involving solvent casting, spin coating, solvent spraying, dipping, fiber forming, ink jet techniques and the like.

Also, while it is preferred that the implant device be realized by a simple tubular structure, it will be recognized that adaptations may be made of such structures. For example, other duct forming structures and shapes can be used. In another example, the device may include holes through the side wall of the tubular structure. In another example, the tubular structure may include multiple lumens therein.

It is also preferred that the elongate tubular structure be constructed of a soft and flexible material that allows for compression of the tubular structure at sufficiently high ocular pressures to provide for a fluid path between the needle tract through the sclera and the compressed tubular structure and out into the surrounding ocular tissue (e.g., the Tenon's membrane pouch as described herein). This releases pressure from the anterior chamber of the eye, for example, in the event that the lumen of the elongate tubular structure is clogged. When the ocular pressure drops to normal levels, the tubular structure returns to its normal uncompressed state and the fluid path through the needle tract is sealed.

Alternatively, the elongate tubular structure might possibly be constructed without a lumen and made sufficiently compressible such that aqueous humor will compress the tubular structure and travel between the compressed tubular structure and the needle tract in order to release pressure from the anterior chamber of the eye. In either configuration, the compressible tubular structure cooperates with the needle tract to provide a pressure relief valve for aqueous humor within the anterior chamber of the eye.

It will therefore be appreciated by those skilled in the art that yet other modifications could be made to the provided invention without deviating from its spirit and scope as claimed.

What is claimed is:

1. An aqueous humor drainage device comprising:
an elongate duct structured to provide a fluid passageway for diverting aqueous humor from the anterior chamber of the eye, said elongate duct having a proximal end opposite a distal end, said proximal end operably disposed within the anterior chamber of the eye and said distal end operably disposed posterior to the limbus of the eye for outlet to a drainage bleb that forms adjacent thereto, said elongate duct formed of a polymeric material comprising polyisobutylene and a glassy segment, said polymeric material having a hardness less than Shore 80A, wherein said elongate duct defines a lumen channel having a diameter between 0.002 in and 0.006 in, and wherein said polymeric material resists obstruction of the elongate duct by tissue encapsulation.

2. An aqueous humor drainage device according to claim 1, wherein:
said polymeric material is loaded with at least one therapeutic agent that minimizes fibrosis of ocular tissue.

3. An aqueous humor drainage device according to claim 2, wherein:
said at least one therapeutic agent is selected from the group including an agent containing verteporfin, an agent containing ranibizumab, an agent containing combretastatin, an agent containing tin ethyl etiopurpurin, an agent containing hydrochlorothiazide and telmisartan, an agent that binds or inhibits Vascular Endothelial Growth Factor, an agent containing Taporfin Sodium, an agent carrying the Pigment Epithelium-Derived Factor (PEDF) gene, an agent carrying endostatin and angiostatin, Integrin, an agent containing 2-methoxyestradiol, Anecortave Acetate, an agent that inhibits Angiotensin II, an agent containing isotretinoin, an agent containing PEGylated aptamer, an agent containing Motexafin, lutetium, mitomycin C, 5-fluorouracil, corticosteroids, modified toxins, methotrexate, adriamycin, radionuclides, protein kinase inhibitors, nitric oxide releasing compounds or analogs or functional equivalents thereof, paclitaxel or analogs or functional equivalents, inhibitors of specific enzymes, superoxide dismutase inhibitors, terminal deoxynucleotidyl-transferas, reverse transcriptase, antisense oligonucleotides that suppress cell proliferation, angiogenesis inhibitors, rapamycin, cerivastatin, and flavopiridol and suramin and the like, peptidic or mimetic inhibitors, pericytes, growth factors, homing receptors, extracellular matrix receptors, subfragments of heparin, triazolopyrimidine, lovastatin, and prostaglandins E1 or I2.

4. An aqueous humor drainage device according to claim 1, wherein:
said glassy segment does not contain any cleavable group which will release in the presence of body fluid inside the human eye and cause toxic side effects and cell encapsulation.

5. An aqueous humor drainage device according to claim 1, wherein:
said glassy segment comprises a vinyl aromatic polymer.

6. An aqueous humor drainage device according to claim 5, wherein:
said vinyl aromatic polymer comprises at least one of styrene and α-methylstyrene.

7. An aqueous humor drainage device according to claim 1, wherein:
said glassy segment comprises a methacrylate polymer.

8. An aqueous humor drainage device according to claim 7, wherein:
said methactylate polymer comprises at least one of methylmethacrylate, ethylmethacrylate, and hydroxymethalcrylate.

9. An aqueous humor drainage device according to claim 1, wherein:
said polymeric material has a general block structure with a central elastomeric polyolefinic block and thermoplastic end blocks.

10. An aqueous humor drainage device according to claim 9, wherein:
said polymeric material comprises a triblock polymer backbone comprising polystyrene-polyisobutylene-polystyrene.

11. An aqueous humor drainage device according to claim 1, wherein:
said polymeric material has a general block structure selected from one of the following:
a) BAB or ABA,
b) B(AB)n or a(BA)n, and
c) X-(AB)n or X-(BA)n;
where A is an elastomeric polyolefinic block, B is a thermoplastic block, n is a positive whole number and X is a starting seed molecule.

12. An aqueous drainage device according to claim 11, wherein:
said material comprises one of a star-shaped block copolymer (where n=3 or more) and multi-dendrite-shaped block copolymer.

13. An aqueous humor drainage device according to claim 1, wherein:
said elongate duct has an outside diameter less than 0.02 inches.

* * * * *